Figure 1:
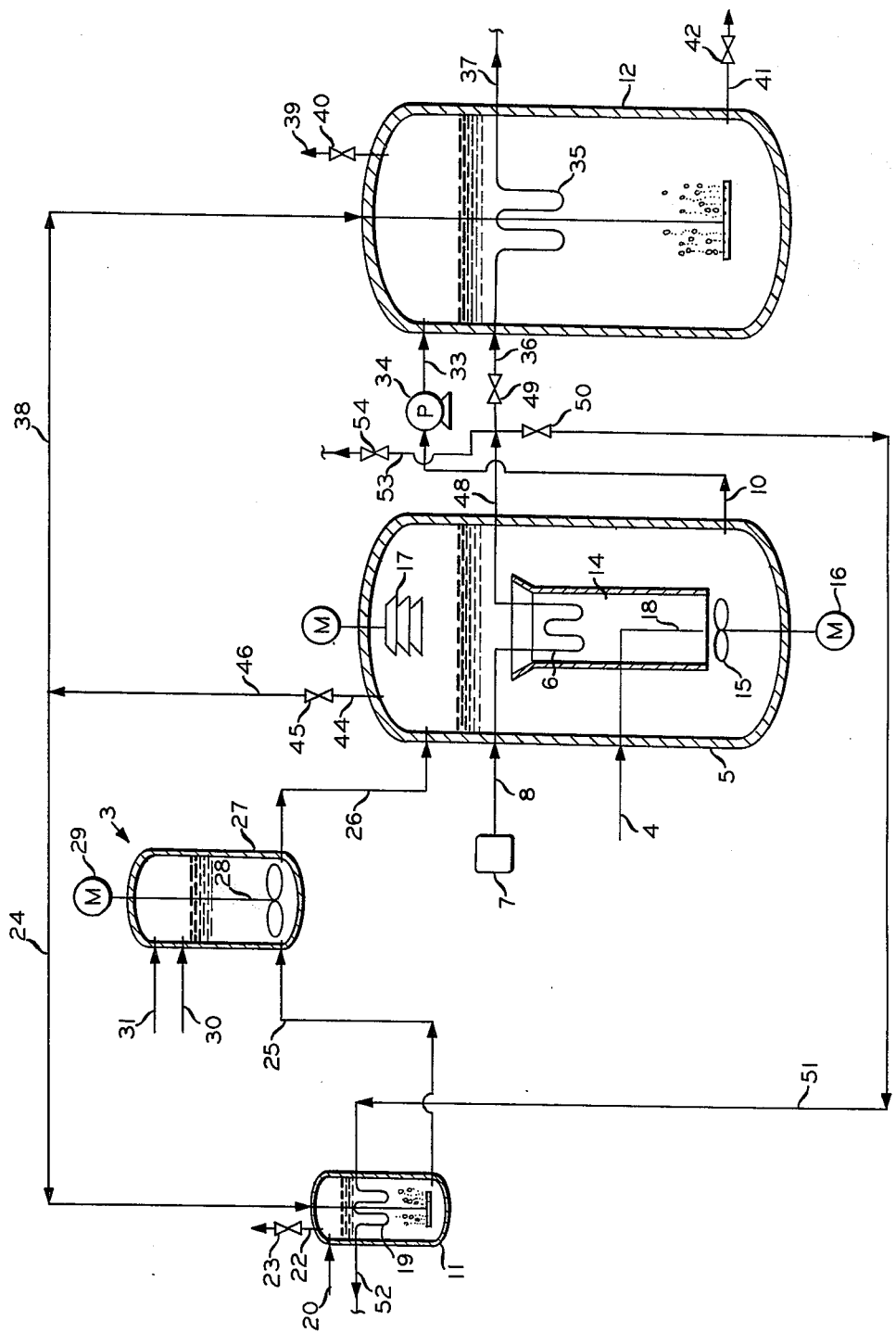

United States Patent [19]

Malick

[11] 3,984,286

[45] Oct. 5, 1976

[54] APPARATUS AND METHOD FOR CONDUCTING FERMENTATION

[75] Inventor: Emil A. Malick, Bartlesville, Okla.

[73] Assignee: Phillips Petroleum Company, Bartlesville, Okla.

[22] Filed: Mar. 6, 1975

[21] Appl. No.: 555,990

[52] U.S. Cl. .............................. 195/141; 195/142; 195/143; 195/109
[51] Int. Cl.² ........................................ C12B 1/16
[58] Field of Search ................. 195/28 R, 115, 142, 195/109, 141, 143

[56] References Cited
UNITED STATES PATENTS

| | | | |
|---|---|---|---|
| 2,244,902 | 6/1941 | Stich | 195/109 |
| 3,032,476 | 5/1962 | Sher | 195/115 |
| 3,041,181 | 6/1962 | Simonin et al. | 195/109 |
| 3,057,785 | 10/1962 | Olsen | 195/142 |
| 3,236,744 | 2/1966 | Yamaha | 195/143 |
| 3,402,104 | 9/1968 | Gore et al. | 195/115 |
| 3,630,848 | 12/1971 | Lefrancois | 195/142 |
| 3,660,244 | 5/1972 | Che | 195/143 |

Primary Examiner—Alvin E. Tanenholtz

[57] ABSTRACT

An apparatus and method for microbial growth by fermentation with the apparatus including a plurality of vessels connected in series. The fermentation vessels include a prefermenter which feeds microorganism-containing effluent continuously to an intermediate fermenter in which the majority of fermentation is conducted. The intermediate fermenter feeds microorganism-containing effluent to a secondary fermenter in which portions of the feedstock are consumed substantially to extinction. Preferably heat exchangers for each of the vessels are connected in series and an oxygen-containing gas which is partially depleted of oxygen can be fed from the intermediate fermenter to the other fermenters in series.

1 Claim, 1 Drawing Figure

APPARATUS AND METHOD FOR CONDUCTING FERMENTATION

In recent years there has been an increase in interest in fermentation processes for making various products such as for the production of low cost edible protein. Thus, interest is being shown, for example, in fermentation processes for culturing microorganisms on relatively less expensive substrates such as n-paraffins, gas-oil, natural gas, methanol and the like. It is believed that protein from single cells offers a good hope for a major new protein supply which is independent of agricultural land use. This is particularly important now because of the rapidly growing world population and recent dramatic shortages in the usual sources of inexpensive protein which have resulted in a new urgency for the commercial development of fermentation processes for the production of single cell protein. This is especially true for developing nations where the usual sources of edible protein are typically in short supply.

Generally, the production of single cell protein is achieved by culturing suitable microorganisms such as bacteria, yeast, fungi and the like in an aerobic fermentation process. Such a process requires the presence of a suitable feedstock or substrate to provide a source of carbon and energy for the microorganisms. In addition, the feedstock includes mineral nutrients, such mineral nutrients usually comprise a source of phosphate, magnesium, calcium, sodium with lesser amounts of copper, manganese and molybdenum ions. The feedstock also includes an assimilible source of nitrogen such as in the form of ammonia. Fermentation processes of interest are aerobic processes wherein relatively large amounts of oxygen are required for the culturing of the microorganisms. In present processes, after a suitable microbial cell growth has been obtained, the fermenter effluent is discharged to cell recovery steps such as centrifuging or filtering to recover the cells which steps are followed by washing and drying steps. From an economic standpoint, it is desirable that the vessels employed in fermentation processes, including the production of single cell protein, be of high productivity, i.e., rapid reactions such as rapid cell growth are highly desirable. High oxygen transfer rates are required for rapid growth of single cell protein and this factor has received considerable effort in the development of fermenter vessels capable of achieving the necessary high oxygen transfer rates. It has been found that the use of a fermenter which operates essentially foam-filled is one type which is able to provide the desired high oxygen transfer rates. A foam-filled fermenter can be obtained by the use of suitable stirring and circulation means with or without added surfactants and with sufficiently high aeration rates. Also, high productivity has required the design of fermenters which are capable of efficient heat removal because of the exothermic nature of the fermentation process. One type of fermenter which can be employed in a foam fermentation process is an essentially cylindrical vessel equipped with a centrally located draft tube having a turbine mixer located at the bottom of the draft tube wherein ferment circulates downwardly through the draft tube and upwardly through a flow path between the draft tube and the interior of the fermenter. The ferment can be passed through openings at the bottom of the draft tube by the mixer to aid in emulsification (foaming) and mixing of the contents therein. It is desirable to provide such a fermenter with a mechanical foam-breaking device located adjacent to the top of the fermenter and which is operable for separating the foam into its gaseous and liquid phases. In spite of the usefulness of such foam-filled fermenters, it is desirable to reduce the power cost in the operation of same and also reduce the cost of cooling such fermenters.

The principal objects of the present invention are: to provide a method and apparatus for conducting fermentation processes which have a relatively high operating efficiency; to provide such an apparatus which includes a plurality of fermenters connected in series wherein each fermenter can be operated at or near its optimum operating conditions which may be different from fermenter to fermenter; to provide such an apparatus which makes efficient use of coolant preferably requiring reduced coolant flow volume; to provide such an apparatus which makes efficient use of oxygen; to provide such an apparatus which effects more complete utilization of components of feedstocks supplied to the fermenters for the microbial growth; to provide such an apparatus which has improved productivity for a given fermenter size; and to provide such an apparatus and method which is well adapted for its intended use and simple in construction and operation.

Other objects and advantages of the present invention will become apparent from the following description taken in conjunction with the accompanying drawings wherein are set forth by way of illustration and example certain embodiments of the present invention.

FIG. 1 is a diagrammatic illustration of a fermentation apparatus.

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting but merely as a basis for the claims and as a representative basis for teaching one skilled in the art to variously employ the present invention in virtually any appropriate detailed structure.

Referring more in detail to the drawings:

The reference numeral 1 designates generally a fermentation apparatus comprised of a plurality of fermentation vessels or fermenters connected in series whereby effluent from one flows to an adjacent downstream fermenter. Means 3 is provided and communicate with at least one of the fermenters and is operable to supply feedstock thereto with the feedstock being comprised of materials necessary for the growth of microorganisms. Oxygen supply means 4 communicate with at least one of the fermenters and is operable to supply oxygen thereto. The plurality of fermenters includes a main or intermediate fermenter 5 in which a majority of the fermentation or microbial growth is conducted. Heat exchange means 6 is in heat transfer relation with at least the main fermenter 5 and is operable to maintain the ferment media therein at a preselected temperature. The heat exchange means 6 is connected to a source 7 of coolant by a conduit 8. Effluent containing microorganisms is discharged from the main fermenter 5 by a discharge 10.

In the illustrated structure, the fermentation apparatus 1 includes a plurality of fermenters which includes a prefermenter 11 connected to the main fermenter 5 and operable to supply microorganism-containing effluent therefrom to the main fermenter. A secondary fermenter 12 is connected to the main fermenter 5 and is operable to receive microorganism-containing effluent from the main fermenter 5. With respect to flow of effluent, the prefermenter 11 is upstream of the main fermenter 5 which is upstream of the secondary fermenter 12. The main fermenter 5, prefermenter 11 and secondary fermenter 12 are of any suitable structure as is known in the art such as cylindrical in shape. Preferably, the prefermenter is of a smaller volume than the main fermenter 5 as, for example, having one-third to one-tenth of the volume of the main fermenter 5.

The main fermenter 5 includes circulation inducing means which are operable to effect circulation of ferment within the main fermenter 5. As shown, a draft tube 14 is suitably mounted within the main fermenter 5 and has an impeller type circulation inducing means or pump 15 which is power operated such as by being operably connected to a motor 16 which, when operated, effects flow of ferment through the draft tube 14 and through a flow path defined by the draft tube and the interior of the main fermenter 5. Although desirable, but not necessary, a foam breaking device 17 is provided such as by mounting within the main fermenter 5 which, when in a foam type fermentation process, is operable to separate the foam into a liquid phase and a gas phase. As shown, the oxygen supply means 4 communicates with the interior of the main fermenter 5 and has a conduit portion 18 positioned so as to discharge oxygen into the ferment adjacent the impeller 15 so as to effect good mixing of the oxygen and ferment. The term "oxygen" as used herein, means any suitable form of oxygen or oxygen-containing gas such as air or oxygen-enriched air.

The prefermenter 11 preferably includes a heat exchanger 19 in heat transfer relation therewith and is connected to a source of coolant such as the source 7 in a manner later described. Feedstock, as described above, is supplied to the prefermenter 11 by an inlet 20 or alternately can be taken from the main fermenter 5 by means (not shown). As shown, the prefermenter 11 includes a vent open to the atmosphere with the vent 22 having a valve such as a pressure relief valve 23 to control the discharge of gas therefrom. The gas is an oxygen-containing gas which is either partially or totally depleted of oxygen used in the microbial growth and introduced into the prefermenter 11 by a conduit 24 which is connected to a suitable source of oxygen. The prefermenter 11 is provided with a discharge 25 which communicates with the main fermenter 5. The position of withdrawal of effluent from the prefermenter 11 by the discharge 25 can be at a position as is dictated by the particular fermentation process such as from the bottom of the prefermenter 11 as is shown or any other suitable position. As shown, the feedstock feed means 3 is connected to the discharge 25 to receive effluent from the prefermenter 11 with the feedstock feed means 3 also communicating with the main fermenter 5 via a conduit 26. The illustrated feedstock feed means 3 comprises a vessel 27 into which component parts of the feedstock are fed and mixed by a suitable mixing device 28 which is power operated such as by a motor 29. As shown, a conduit 30 opens into the vessel 27 and supplied the carbon and energy source portion of the feedstock and a conduit 31 opens into the vessel 27 and is operable to supply an aqueous mixture of minerals and other nutrients which preferably includes an assimilible source of nitrogen such as ammonia. It is to be noted that oxygen can also be supplied to the vessel 27 by suitable means if desired.

The use of feedstock means as shown effects mixing of the component parts of the feedstock and also the mixing of oxygen therewith, if desired, before the feedstock enters the main fermenter 5 thereby not requiring any residence time within the main fermenter to effect the mixing of same with effluent which flows from the prefermenter 11 to the main fermenter 5.

The main fermenter 5, has the discharge 10 thereof, connected to the secondary fermenter 12 such as by a conduit 33. If desired pump means 34 can be provided to communicate with the discharge 10 and help induce flow of effluent from the main fermenter 5 to the secondary fermenter 12. The position of discharge of effluent from the main fermenter 5 can be at any suitable position such as adjacent the lower end, as is shown, or any other suitable position as is dictated by the particular fermentation process and effluent desired to be discharged. Preferably, the secondary fermenter 12 includes a heat exchanger 35 in heat transfer relation thereto which is connected to a source of coolant such as by a conduit 36. Coolant from the heat exchanger 35 is discharged through a conduit 37. It is preferred that oxygen from a suitable source be supplied to the secondary fermenter such as via a conduit 38 which is also connected to the source of oxygen. A vent 39 communicates with the secondary fermenter 12 and preferably has a pressure relief valve 40 cooperating therewith to control the discharge of gas therefrom. The discharged gas is that which is introduced into the secondary fermenter 12 via the conduit 38 and is partially or totally depleted of oxygen. The secondary fermenter is also provided with a discharge 41 which communicates with the interior of the secondary fermenter 12 at a position suitable for the removal of the desired effluent with the position being dictated by the particular fermentation process and the desired effluent to be discharged. The discharge 41 as shown has a valve 42 which is operable to control the rate of discharge of effluent. Effluent discharged through the discharge 41 then passes to other equipment (not shown) for further processing of the effluent, i.e., cell recovery steps such as centrifuging or filtering to recover the cells which is followed by washing and drying steps.

It is to be noted that the prefermenter 11 and the secondary fermenter 12 are characterized as being preferably of simpler construction than the main fermenter 5 in which the majority of the fermentation process is conducted as described below. As shown, the source of oxygen for the prefermenter 11 and secondary fermenter 12 is supplied from the oxygen supply 4 with the oxygen or oxygen-containing gas taken from the main fermenter 5 adjacent the uppermost disposed portion thereof through a vent 44. A suitable valve 45 such as a pressure relief valve or flow control valve is connected to the vent 44 to control the flow of the oxygen-containing gas which is partially depleted of oxygen due to consumption of oxygen by the fermentation in the main fermenter 5. The conduits 24 and 38 are connected to a conduit 46 which is connected to the outlet of the valve 45. Such an arrangement provides the series use of oxygen as described below. It is preferred that coolant from the source 7, after same has passed through the heat exchange means 6, be discharged through a discharge conduit 48 and used to cool the remaining fermenters. The heat exchangers 35 and 19 can be connected in series or, as shown, they are each connected only in series with the heat exchange means 6 whereby a portion of the coolant flows through a flow regulating valve 49 into the conduit 36 and then through the heat exchanger 35. The remaining portion of the coolant flows through a flow regulating valve 50 which is connected to the discharge 48 and into a conduit 51 for flow to and through the heat exchanger 19 and out a discharge 52. In a closed heat exchange system, the coolant from the discharges 37 and 52 would be recirculated to a suitable refrigeration means (not shown) and returned to the source 7. Such an arrangement of heat exchangers permits the series use of coolant. The flow control valves 49 and 50 can be automatically or manually controlled but preferably, automatically, with same functioning in response to temperature changes within the respective fermenters to control the temperature therein and at a preselected temperature. It is to be noted that if there is an overabundance of coolant discharged through the discharge 48, that is not needed for cooling the prefermenter 11 and secondary fermenter 12, same can be returned to the source 7 after refrigeration through a conduit 53 which has a control valve 54 and other means (not shown).

The present invention is more fully understood by a description of the operation thereof. Preferably, the fermentation apparatus 1 is of a continuous operating type which employs a foam-filled fermenter as the main fermenter 5. The fermentation process is carried out by the use of the prefermenter 11 in which the microbial growth is started and at a suitable cell concentration a portion of the contents are discharged as microorganism-containing effluent, preferably continuously to the main fermenter 5. Before being introduced into the main fermenter 5 the effluent from the prefermenter 11 has feedstock and preferably oxygen introduced thereinto and mixed before introduction into the main fermenter 5. Preferably, the effluent from the prefermenter is at a cell concentration which is at the stage of rapid growth, that is when the cell concentration in the primary fermenter is rapidly increasing. Thus, high oxygen transfer rates and high heat exchange rates are not necessary in the prefermenter. It is to be noted also that the conditions in the prefermenter 11 can be controlled to optimize the initial growth of the microorganism which may or may not be different than the conditions necessary for a rapid growth rate. The microorganism-containing effluent transferred to the main fermenter then continues to grow with the aid of the high oxygen transfer capabilities and heat removing capacity of the main fermenter 5. Thus, it is seen that the main fermenter 5 can be operated at conditions to effect high growth rates with such conditions including the amount of the different components in the feedstock and the operating temperature and oxygen transfer rates. The main fermenter 5 is operated at a predetermined cell concentration with a portion of the ferment being discharged through the discharge 10 as microorganism-containing effluent which is then transferred to the secondary fermenter 12. The microbial growth can be continued in the secondary fermenter 12 to finally consume the remaining feedstock to substantial extinction. Effluent from the secondary fermenter 12 is discharged through the discharge 41 with a minimum of feedstock components contained therein. The conditions in the secondary fermenter 12 can be maintained to optimize the consumption of the feedstock components. Thus, it is seen that each of the fermenters can be operated at different conditions most suitable for the particular growth stage and thereby optimize the total process. For a given set of fermentation conditions suitable for the production of a given cell concentration, the use of the apparatus 1 provides a reduction in the time required for the fermentation to remain in the main fermenter 5 and also a reduction in the amount of heat which must be removed in the main fermenter 5. It is desirable in fermentation processes to consume all the carbon and energy source to avoid having same in the effluent product so as to eliminate the need for processing steps to separate the carbon and energy source from the effluent. With the apparatus as shown, the main fermenter 5 can be operated at higher than normal concentrations of the carbon and energy source to optimize and enhance the fast growth rate in the main fermenter 5 whereby the excess carbon and energy source is passed to the secondary fermenter 12 for consumption to substantial extinction.

It is to be understood that while I have illustrated and described certain forms of my invention, it is not to be limited to the specific form or arrangement of parts as herein described and shown.

What is claimed and desired to be secured by Letters Patent is:

1. An apparatus for microbial growth by fermentation, said apparatus comprising:
   a. a prefermenter;
   b. an intermediate fermenter connected in series, by a first conduit, with and downstream of said prefermenter, whereby effluent from said prefermenter is fed to said intermediate fermenter, said intermediate fermenter having a volume substantially larger than said prefermenter;
   c. a draft tube mounted in said intermediate fermenter;
   d. an impeller positioned adjacent said draft tube and operable to effect flow of media through said draft tube;
   e. first heat exchange means in heat transfer relation with said intermediate fermenter and connected to a source of coolant;
   f. a secondary fermenter connected in series by a second conduit with and downstream of said intermediate fermenter whereby effluent from said intermediate fermenter is fed to said secondary fermenter;
   g. first means communicating with said intermediate fermenter and operable for introducing feedstock and oxygen into said intermediate fermenter;
   h. second heat exchange means in heat transfer relation with said secondary fermenter and is connected in series with and downstream of said first heat exchange means;
   i. third heat exchange means in heat transfer relation with said prefermenter and is connected in series with and downstream of said first heat exchange means;
   j. a second conduit connecting said intermediate fermenter with said secondary fermenter and forming a flow path therebetween for conducting oxygen from said intermediate fermenter to said secondary fermenter;
   k. a third conduit communicating between said intermediate fermenter and said prefermenter forming a flow path for conducting oxygen from said intemediate fermenter to said prefermenter; and
   l. a vessel communicating with said first conduit between said prefermenter and said intermediate fermenter wherein effluent from said prefermenter flows into said vessel before flowing into said intermediate fermenter with said vessel having mixing means operably associated therewith and also having inlet means opening thereinto.

* * * * *